United States Patent [19]

Collins et al.

[11] Patent Number: 5,089,524

[45] Date of Patent: Feb. 18, 1992

[54] TETRAENYL PROSTANOIC ACID DERIVATIVES AS PRODRUGS FOR THE TREATMENT OF PEPTIC ULCER DISEASE

[75] Inventors: Paul W. Collins, Deerfield; Alan F. Gasiecki, Vernon Hills, both of Ill.

[73] Assignee: G. D. Searle & Co., Chicago, Ill.

[21] Appl. No.: 546,218

[22] Filed: Jun. 28, 1990

[51] Int. Cl.$^5$ .................. C07C 177/00; A61K 31/557
[52] U.S. Cl. .................. 514/530; 514/573; 560/118; 560/121; 560/231; 562/500; 562/503
[58] Field of Search .......... 560/118, 121, 231; 562/500, 503; 514/530, 573

[56] References Cited

U.S. PATENT DOCUMENTS 4,683,328 7/1987 Collins .................. 560/118
4,847,293 7/1989 Collins .................. 560/118

Primary Examiner—Robert Gerstl
Attorney, Agent, or Firm—Roger A. Williams; Paul D. Matukaitis

[57] ABSTRACT

Tetraenyl Prostanoic Acid derivatives which are useful as prodrugs for the treatment of peptic ulcer disease and are represented by the following general formula

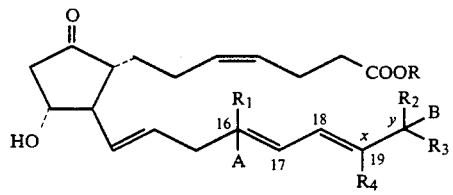

are disclosed.

11 Claims, No Drawings

TETRAENYL PROSTANOIC ACID DERIVATIVES AS PRODRUGS FOR THE TREATMENT OF PEPTIC ULCER DISEASE

BACKGROUND OF THE INVENTION

This invention relates to a novel class of prostanoic acid derivatives, to a method of treating peptic ulcer disease, and to pharmaceutical compositions containing these derivatives.

It is known that certain prostaglandins have been found to be useful in the treatment of peptic ulcer disease. It is further known that a specific class of these prostaglandins, namely tetraenyl, 16-hydroxy prostaglandins which are represented by the following structural formula

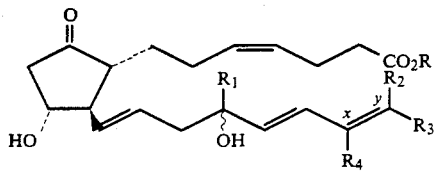

wherein R represents hydrogen or lower alkyl having 1 to 6 carbon atoms; $R_1$ represents vinyl, or lower alkyl having 1 to 4 carbon atoms and the wavy line represents R or S stereochemistry; $R_2$, $R_3$ and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons have potent gastric antisecretory and cytoprotective properties which makes them effective in the treatment of peptic ulcer disease. These compounds are described further in U.S. Pat. No. 4,683,328.

Applicants have discovered that certain 16-alkyl tetraenyl prostanoic acid derivatives which are represented by formula I function as in vivo precursors or pro drugs of the aforementioned 16-hydroxy tetraenyl prostanoic acid derivatives which are represented by formula IV (Scheme A). In order for the compounds of formula I to exert their antisecretory and cytoprotective properties they must be "transformed" into the active species which are represented by formula IV. This "transformation" takes place in an acidic medium. Thus the pro drugs must be administered by a method that would allow for exposure to said condition.

Detailed Description of the Invention

The specific prodrugs of this invention are the compounds represented by the following structural formula

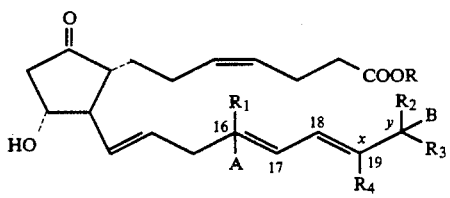

or a pharmaceutically acceptable base addition salt when R is hydrogen thereof:
wherein R is hydrogen or alkyl having 1 to 6 carbon atoms; $R_1$ is alkyl having 1 to 6 carbon atoms; $R_2$, $R_3$ and $R_4$ are each independently hydrogen or alkyl having 1 to 4 carbon atoms or $R_3$ and $R_4$ together with carbons X and Y form a cycloalkyl having 4 to 6 carbon atoms or a cycloalkenyl having 4 to 6 carbon atoms with the proviso that the cycloalkenyl group is only present when A is present; A is an optionally present alkoxy group having 1 to 6 carbon atoms with the proviso that when A is present the double bond at carbon 16 and carbon 18 of formula I shifts to carbon 17 and carbon 19, respectively; B is an optionally present group represented by the following formula

wherein $R_5$ is hydrogen, alkyl having 1 to 4 carbon atoms or acyl which is represented by the following formula

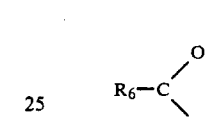

wherein $R_6$ is alkyl having 1 to 6 carbon atoms with the proviso that B is present when A is not present.

A preferred embodiment of the present invention are compounds of the formula

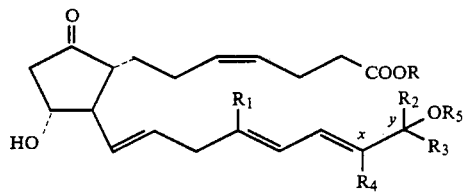

wherein R is alkyl having 1 to 6 carbon atoms; $R_1$ is alkyl having 1 to 6 carbon atoms; $R_2$ is hydrogen; $R_3$ and $R_4$ together with carbon X and Y form a cycloalkyl having 4 to 6 carbon atoms; $R_5$ is hydrogen, alkyl having 1 to 4 carbon atoms or acyl which is represented by the following formula

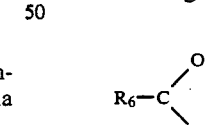

wherein $R_6$ is alkyl having 1 to 6 carbon atoms. Exemplifying this embodiment are the following compounds (±)-methyl 7-[3α-hydroxy-2β-[6-(2-hydroxy-Z-cyclopentylidine)-4-methyl-1E,4E-hexadienyl]-5-oxo-1α-cyclopentyl]-4Z-heptenoate and (±)-methyl 7-[2β-(6-(2-(acetyloxy)-Z-cyclopentylidine]-4-methyl-1E,4E-hexadienyl]-3α-hydroxy-5-oxo-1α-cyclopentyl]-4Z-heptenoate Another preferred embodiment of the present invention are compounds of the formula

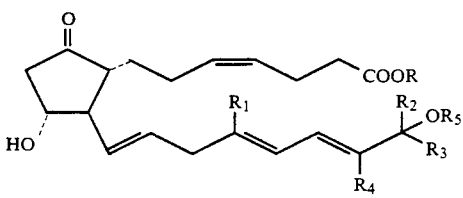

wherein R is alkyl having 1 to 6 carbon atoms; $R_1$ is alkyl having 1 to 6 carbon atoms; $R_2$, $R_3$ and $R_4$ are each independently hydrogen or alkyl having 1 to 4 carbon atoms; and $R_5$ is hydrogen, alkyl having 1 to 4 carbon atoms or acyl which is represented by the following formula

wherein $R_6$ is alkyl having 1 to 6 carbon atoms.

Exemplifying this embodiment are the following compounds (±)-methyl 7-[3α- hydroxy-2β-(8-hydroxy-4,8-dimethyl-1E,4,6-nonatrienyl)-5-oxo-1α-cyclopentyl]-4Z-heptenoate and (±)-methyl 7-[3α- hydroxy-2β-(8-methoxy-4,8-dimethyl-1E,4,6-nonatrienyl)-5-oxo-1α-cyclopentyl]-4Z-heptenoate A further preferred embodiment of the present invention are compounds of the formula

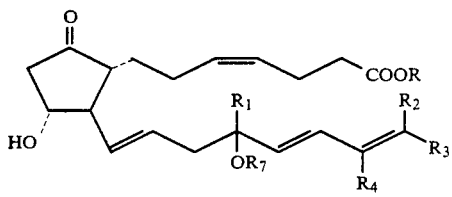

wherein R is alkyl having 1 to 6 carbon atoms; $R_1$ is alkyl having 1 to 6 carbon atoms; $R_2$, $R_3$ and $R_4$ are each independently hydrogen or alkyl having 1 to 4 carbon atoms; and $R_7$ is alkyl having 1 to 6 carbon atoms.

Exemplifying this embodiment is the following compound (±)-methyl 7-[2β-(4,8-dimethyl-4-methoxy-1E,5E,7E-nonatrienyl)-3α-hydroxy-5-oxo-1α-cyclopentyl]-4Z-heptenoate As used herein the term "alkyl having 1 to 6 carbon atoms" refers to straight chain or branched chain hydrocarbon groups having from one to six carbon atoms. Illustrative of such alkyl groups are methyl, ethyl, propyl, isopropyl, butyl, isobutyl, pentyl, neopentyl, hexyl and isohexyl.

As used herein the term "cycloalkyl having from 4 to 6 carbon atoms" included cycloalkyl groups having from four to six carbon atoms. Illustrative of such cycloalkyl groups are cyclobutyl, cyclopentyl and cyclohexyl.

As used herein the term "cycloalkenyl having 4 to 6 carbon atoms" included cycloalkenyl groups having from four to six carbon atoms. Illustrative of such cycloalkenyl groups are cyclobutenyl, cyclopentenyl and cyclohexenyl.

As used herein the term "alkoxy wherein the alkyl is 1 to 6 carbon atoms" refers to straight or branched chain ethers. Illustrative of such groups are methoxy, ethoxy, propoxy, butoxy, isopropoxy and the like.

Compounds of general Formula I can possess one or more asymmetric carbon atoms and are thus capable of existing in the form of optical isomers as well as in the form of racemic or diastereoisomeric mixtures thereof. The optical isomers and mixtures thereof can be obtained by processes described in U.S. Pat. Nos. 4,683,328 and 4,863,961, by formation and chromatographic separation of diastereoisomeric derivatives and then regeneration of the resolved product.

Within this class of prostaglandin, compounds and derivatives of the invention are the pharmaceutically-acceptable salts of the compounds of Formula I when R=H. The term "pharmaceutically-acceptable salts" embraces salts commonly used to form alkali metal salts. The nature of the salt is not critical, provided that it is pharmaceutically-acceptable. Suitable pharmaceutically-acceptable base addition salts of compounds of Formula I include alkali metal salts, e.g., salts of sodium and potassium, and ammonium salts and amine salts. All of these salts may be prepared by conventional means from the corresponding compound of Formula I by reacting, for example, the appropriate base with the compound of Formula I.

The compounds of formula (I) may be prepared in accordance with the following procedures:

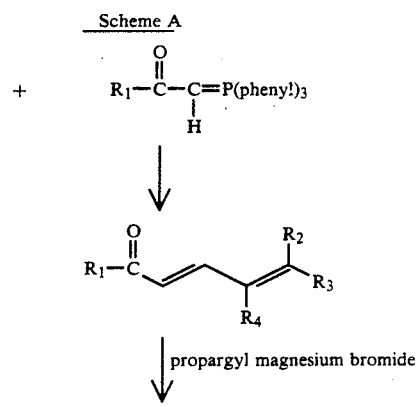

-continued
Scheme A
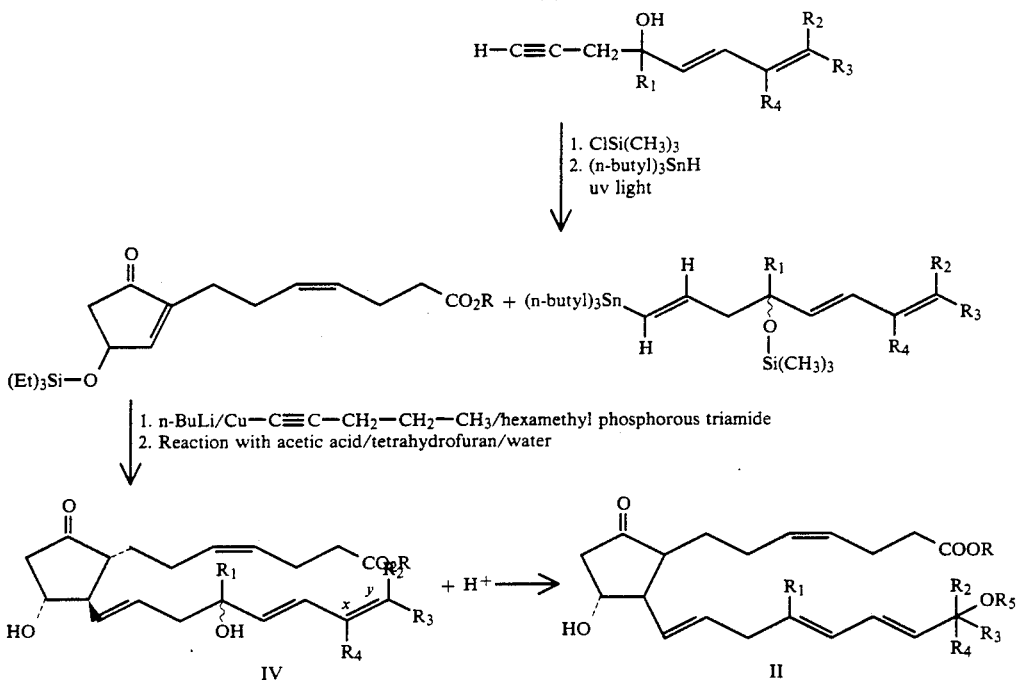
wherein R, $R_1$, $R_2$, $R_3$, $R_4$ and $R_5$ are defined as before. This general reaction as well as specific preparations of compounds encompassed by Formula IV are described in U.S. Pat. No. 4,683,328. Compounds of formula IV will undergo acid catalyzed allylic rearrangement to give the compounds of formula II:
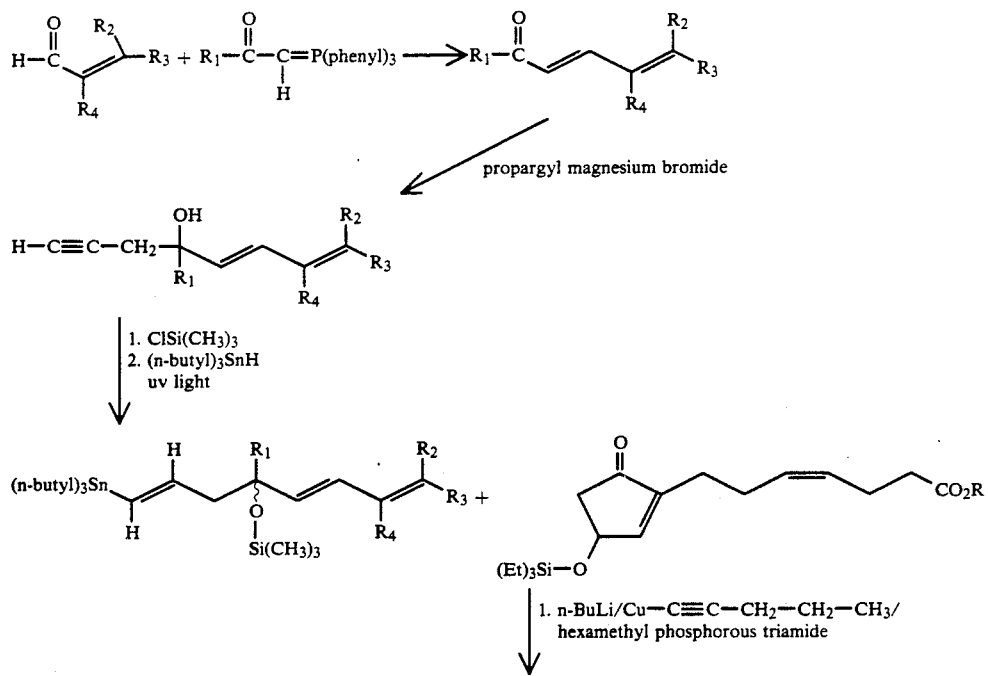

-continued
Scheme B

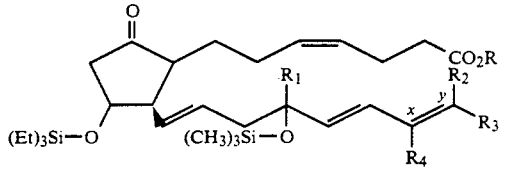

+ pyridinium p-toluenesulfonate

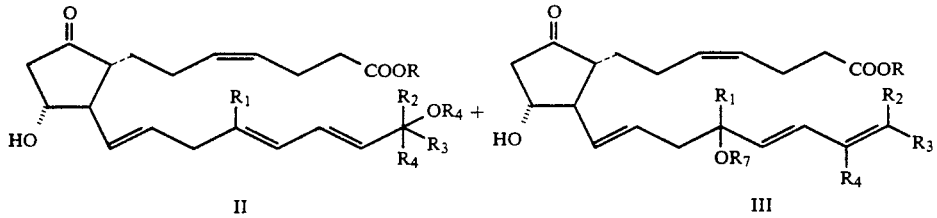

wherein R, $R_1$, $R_2$, $R_3$, $R_4$, $R_5$ and $R_7$ are defined as before. Scheme B follows the Scheme A synthetic route to the preparation of the di-silylated precursors of Formula IV, Scheme A. The di-silylated intermediates are then treated with pyridinium p-toluenesulfonate to give the compounds of Formula II and Formula III which are separated by chromatographic methods.

This invention also relates to a method of treatment for subjects suffering from peptic ulcer disease, and more specifically, a method of treatment involving the administration of compounds which are represented by formula I as the active ingredient. The compounds of the present invention must be administered by an oral route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more nontoxic, pharmaceutically acceptable carriers and/or diluents and/or adjuvants (collectively referred to herein as "carrier" materials) and if desired other active ingredients.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 500 µg, preferably from about 5 to 200 µg. A suitable daily dose for a subject may vary widely depending on the condition of the patient and other factors. However, a dose of from about 0.01 to 1000 ug/kg body weight, particularly from about 0.1 to 100 ug/kg body weight may be appropriate.

For therapeutic purposes, the compounds of this invention are ordinarily combined with one or more adjuvants appropriate to the indicated route of administration. For per os administration, the compounds may be admixed with lactose, sucrose, starch power, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration.

Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants are well and widely known in the pharmaceutical art. Appropriate dosages, in any given instance, of course depend upon the nature and severity of the condition treated and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules or powders or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The amount of active ingredient that may be combined with the carrier materials to produce a single dosage form will vary depending upon the host treated. For example, a formulation intended for the oral administration of subjects may contain from 1 µg to 500 µg of active agent compounded with an appropriate and convenient amount of carrier material which may vary from about 5 to 95 percent of the total composition. Dosage unit forms will generally contain between from about 1 µg to about 500 µg of active ingredient.

It will be understood, however, that the specific dose level for any particular patient will depend upon a variety of factors including the activity of the specific compound employed, the age, body weight, general health, sex, diet, time of administration, rate of excretion, drug combination and the severity of the particular disease undergoing therapy.

The following Examples are intended to further illustrate the present invention and not to limit the invention in spirit or scope.

EXAMPLE 1

Preparation of (±)-methyl 7-[3α-hydroxy-2β-(6-(2-hydroxy-Z-cyclopentylidine)-4-methyl-1E,4E-hexadienyl]-5-oxo-1α-cyclopentyl]-4Z-heptenoate

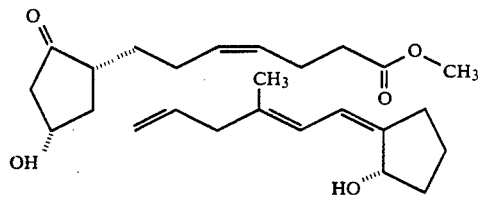

The di-silylated intermediate (±)-methyl 7-[2β-(6-(1-cyclopenten-1-yl)-4-methyl-4-[trimethylsilyl)oxy]-1E,5E-hexadienyl]-5-oxo-3α-[(triethylsilyl)-1α-cyclopentyl]-4Z-heptenoate (830 mg) was dissolved in a mixture of 18 ml of acetone and 2 ml H₂O and 26 mg of pyridinium p-toluenesulfonate (PPTS) was added. The solution was allowed to stand at room temperature for about 24 hours. The solution was reduced in volume on a rotary evaporator and the resulting mixture was diluted with ether and washed with water and then saturated sodium chloride solution. The organic layer was dried over sodium sulfate (Na₂SO₄) and evaporated on a rotary evaporator. The residue was chromatographed on silica gel with 70% ethyl acetate/30% hexane as eluent to give 15 mg of the title compound and 120 mg of a mixture of deprotected starting material.

NMR data for title compound: ¹H (CDCl₃) δ1.77 (s,C-16 CH3); 2.24, 2.75 (multiplets C-10 H's); 2.86 (d C-15 H's); 4.49 (broad, s,C-20 H); 6.37 (d, C-17 H); 5.92 (d, C-18 H). This compound is a mixture of eight isomers at C-16 (E and Z), C-18 (E and Z) and C-20 (R and S).

EXAMPLE 2

Preparation of (±)-methyl 7-[3α-hydroxy-2β-(6-(2-hydroxy-Z-cyclopentylidine)-4-methyl-1E, 4E-hexadienyl]-5 oxo-1α-cyclopentyl]-4Z-heptenoate

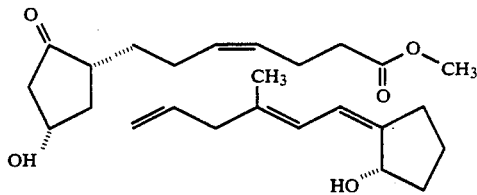

Alternate Method (±)-methyl 7-[2β-(6-(1-cyclopenten-1-yl)-4S-hydroxy-4-methyl-1E,5E-hexadienyl]-3α-hydroxy-5-oxo-1α-cyclopentyl]-4Z-heptenoate (100 mg) dissolved in 2 ml THF was added in one portion to 15 ml of fresh dog gastric juice (pH ~ 1) with stirring. The turbid mixture was stirred for 1 hour at room temperature. The mixture was extracted with ether and then twice with ethyl acetate. The organic extracts were combined, washed with H₂O and then saturated sodium chloride solution, dried (Na₂SO₄) and evaporated. The residue was chromatographed on silica gel using 55% ethyl acetate/45% hexane as eluent to give 3.4 mg of the title compound and a mixture of (±)-methyl 7-[2β-(6-(1-cyclopenten-1-yl)-4R-hydroxy-4-methyl-1E, 5E-hexadienyl]-3α-hydroxy-5-oxo-1α-cyclopentyl]-4Z-heptenoate and (±)-methyl 7-[2β(6-(1-cyclopenten-1-yl)-4S-hydroxy-4-methyl-1E,5E-hexadienyl]-3α-hydroxy-5-oxo-1α-cyclopentyl]-4Z-heptenoate.

NMR data for title compound: ¹H (CDCl₃) δ1.77 (s,C-16 CH3); 2.24, 2.75 (multiplets C-10 H's); 2.86 (d C-15 H's); 4.49 (broad, s,C-20 H); 6.37 (d, C-17 H); 5.92 (d, C-18 H). This compound is a mixture of eight isomers at C-16 (E and Z), C-18 (E and Z) and C-20 (R and S).

EXAMPLE 3

Preparation of (±)-methyl 7-[3α-hydroxy-2β-(8-methoxy-4, 8-dimethyl-1E,4,6-nonatrienyl)-5-oxo-1α-cyclopentyl]-4Z-heptenoate

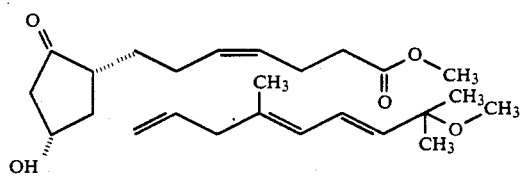

and (±)-methyl 7-[2α-(4,8-dimethyl-4-methoxy-1E,5E-7E-nonatrienyl)-3α-hydroxy-5-oxo-1α-cyclopentyl]-4Z-heptenoate

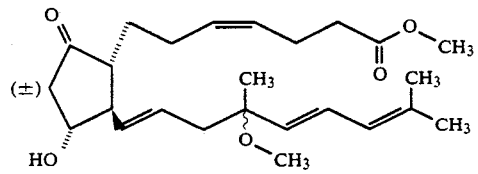

A solution of 92 mg of the disilylated prostaglandin in 4 ml of methanol and several crystals of pyridinium p-toluenesulfonate was allowed to stand at room temperature for 3 hours. The solution was reduced in volume on a rotary evaporator, diluted with ether and washed twice with H₂O, once with saturated NaCl solution, dried (Na₂SO₄) and evaporated. Chromatography of the residue on silica gel with 50% ethyl acetate/50% hexane as eluent gave 13 mg of (±)-methyl 7-[3α-hydroxy-2β-(8-methoxy-4,8-dimethyl-1E,4,6-nonatrienyl)-5-oxo-1α-cyclopentyl]-4Z-heptenoate NMR: ¹H (CDCl₃) δ1.21 (s,C-20 CH3); 3.18 (s,C-20 OCH3); 2.24, 2.76 (m,C-10 H's); 1.79 (s,C-16 CH3); 5.89 (d, C-17 H); 6.37 (dd, C-18 H); 5.59 (d, C-19 H). This compound is an approximate 3:2 mixture of E and Z isomers at C-16.

and 9.1 mg of (±)-methyl 7-[2β-(4,8-dimethyl-4-methoxy-1E,5E,7E-nonatrienyl)-3α-hydroxy-5-oxo-1α-cyclopentyl]-4Z-heptenoate NMR: ¹H (CDCl₃) δ1.28 (s,C-16 CH3); 1.78, 1.79 (s,C-20 CH3); 3.17 (s,C-16 OCH3); 5.45, 5.46 (m,C-17 H); 5.84 (d,C-19 H); 6.34, 6.35 (m,C-18 H).

EXAMPLE 4

Preparation of (±)-methyl 7-[3α-hydroxy-2β-(8-hydroxy-4,8-dimethyl-1E,4,6-nonatrienyl)-5-oxo-1α-cyclopentyl]-4Z-heptenoate

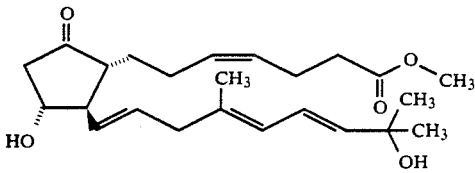

A mixture of (±)-methyl 7-[2β-(4,8-dimethyl-4R-hydroxy-1E,5E,7E-nonatrienyl)-3α-hydroxy-5-oxo-1α-cyclopentyl]-4Z-heptenoate and (±)-methyl 7-[2β-(4,8-dimethyl-4S-hydroxy-1E,5E,7E-nonatrienyl)-3α-hydroxy-5-oxo-1α-cyclopentyl]-4Z-heptenoate (90 mg) was dissolved in a mixture of 6 ml of acetone and 2 drops of 0.5 N HCl and allowed to stand at room temperature for 3 hours. The solution was diluted with ether and washed successively with dilute NaHCO₃ solution and saturated NaCl solution and evaporated. The residue was chromatographed with 65% ethyl acetate/35% hexane as eluent to give 17 mg of the title compound.

NMR: $^1$H(CDCl₃) δ1.35 (s,C-20 CH₃); 1.77 (s,C-16 CH₃); 5.77 (m,C-19 H); 5.86 (m,C-17 H); 5.95 (m,C-18 H).

EXAMPLE 5

Preparation of (±)-methyl 7-[2β-(6-(2-(acetyloxy)-Z-cyclopentylidine]-4-methyl-1E,4E-hexadienyl]-3α-hydroxy-5-oxo-1α-cyclopentyl]-4Z-heptenoate

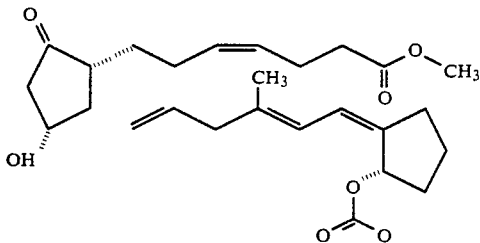

(±)-methyl 7-[2β-(6-(1-cyclopenten-1-yl)-4S-hydroxy-4-methyl-1E,5E-hexadienyl]-3α-hydroxy-5-oxo-1α-cyclopentyl]-4Z-heptenoate (0.13 g) was mixed with 3 ml glacial acetic acid at room temperature and stirred under N₂ for 24 hours. The reaction was quenched by addition of 50 ml saturated NaHCO₃ solution and was extracted with 2 portions of ethyl ether. The combined ether extracts were washed with brine, and dried (Na₂SO₄) Chromatography on silica (45% Ethyl acetate/55% Hexane) gave 52 mg of the title compound.

NMR: $^1$H (CDCl₃) δ2.06 (s,acetyl CH₃); 1.77 (s,C-16 CH₃); 5.49, 5.53 (m,C-20 H); 5.90, 5.94 (d,C-18 H); 6.41, 6.47 (d,C-17 H). This compound is an approximate 4:1 mixture of isomers, probably C-20 R and S diastereomers.

EXAMPLE 6

In vitro regeneration of 16-hydroxy compounds A and B from corresponding prodrug.

(±)-methyl 7-[2β-(4,8-dimethyl-4R-hydroxy-1E,5E,7E-nonatrienyl)-3α-hydroxy-5-oxo-1α-cyclopentyl]-4Z-heptenoate

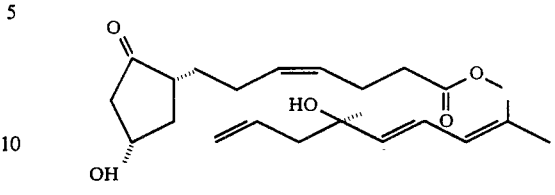

and (±)-methyl 7-[2β-(4,8-dimethyl-4S-hydroxy-1E,5E,7E-nonatrienyl)-3α-hydroxy-5-oxo-1α-cyclopentyl]-4Z-heptenoate

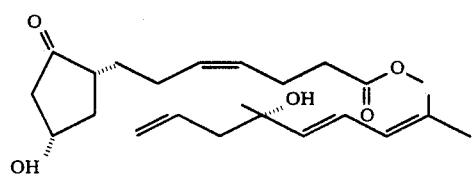

5 mg of the product of Example 4 was dissolved in 1 ml of a 3:1:1 mixture of acetic acid, THF (tetrahydrofuran) and H₂O and allowed to stand about 1 hour at room temperature. Thin layer monitoring with standards of Compounds A and B indicated the generation of the title compounds and the diminishment of starting material.

EXAMPLE 7

(±)-Methyl 7-[3α-hydroxy-2β-[6-(2-hydroxy-Z-cyclopentylidine)-4-methyl-1E,4E-hexadienyl]-5-oxo-1α-cyclopentyl]-4Z-heptenoate (Compound of Example 1), (±)-methyl 7-[3α-hydroxy-2β-(8-hydroxy-4,8-dimethyl-1E,4,6-nonatrienyl-5-oxo-1α-cyclopentyl]-4Z-heptenoate (Compound of Example 4), and (±)-methyl 7-[2β-[6-(2-(acetyloxy)-Z-cyclopentylidine)-4-methyl-1E,4E-hexadienyl]-3α-hydroxy-5-oxo-1α-cyclopentyl]-4Z-heptenoate (Compound of Example 5) were tested for gastric antisecretory activity in the Pavlov Pouch Dog Test. The procedure for this test is described as follows.

Adult female beagles (6-11 kg), with innervated (Pavlov) gastric pouches, were food deprived with access to water 24 h prior to experiments. Following a 30 min basal collection period, the prostaglandin in a buffer/ethanol vehicle was administered into the pouch through a Thomas cannula followed by either a saline or 0.1N HCl flush. Thirty minutes later the gastric pouch was emptied and gastric secretion was stimulated by feeding 10-12 oz of canned dog food (Evanger's Dog and Cat Food Co., Inc., Wheeling, Ill.). Gastric juice samples were collected over a 4 h period at 30 min intervals. Total acid output (mequiv/30 min) was determined for each collection period by multiplying the volume of secretion (mL/30 min) and the acidity (mequiv/L). Percent reduction of total acid output from control was calculated over each 4 h experiment.

The compounds of Example 1, 4 and 5, have the following results:

| Compound of | n | Flush | Dose | % Decrease in 4 hr Total Acid Output |
|---|---|---|---|---|
| Example 1 | 4 | saline | 0.3 μg/kg | 31 |
|  | 2 | 0.1 NHCl | 0.3 μg/kg | 87 |
| Example 4 | 2 | saline | 0.3 μg/kg | 28 |
|  | 2 | 0.1 NHCl | 0.3 μg/kg | 76 |
| Example 5 | 2 | saline | 0.3 μg/kg | 88 |
|  | 2 | 0.1 NHCl | 0.3 μg/kg | 73 |

What we claim is:

1. A compound of the general formula:

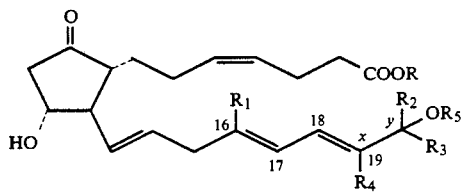

or a pharmaceutically acceptable base addition salt when R is hydrogen thereof:
 wherein R is hydrogen or alkyl having 1 to 6 carbon atoms; $R_1$ is alkyl having 1 to 6 carbon atoms; $R_2$, $R_3$ and $R_4$ are each independently hydrogen or alkyl having 1 to 4 carbon atoms or $R_3$ and $R_4$ together with carbons X and Y form a cycloalkyl having 4 to 6 carbon atoms;
 wherein $R_5$ is hydrogen, alkyl having 1 to 4 carbon atoms or acyl which is represented by the following formula

wherein $R_6$ is alkyl having 1 to 6 carbon atoms.

2. A compound of claim 1 having the following formula

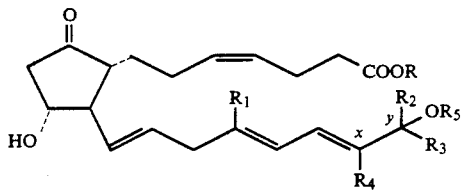

wherein R is alkyl having 1 to 6 carbon atoms; $R_1$ is alkyl having 1 to 6 carbon atoms; $R_2$ is hydrogen; $R_3$ and $R_4$ together with carbon X and Y form a cycloalkyl having 4 to 6 carbon atoms; $R_5$ is hydrogen, alkyl having 1 to 4 carbon atoms or acyl which is represented by the following formula

wherein $R_6$ is alkyl having 1 to 6 carbon atoms.

3. A compound of claim 2 which is
 (±)-methyl 7-[2β-(6-(2-(acetyloxy)-Z-cyclopentylidine]-4-methyl-1E,4E-hexadienyl]-3α-hydroxy-5-oxo-1α-cyclopentyl]-4Z-heptenoate.

4. A compound of claim 2 which is
 (±)-methyl 7-[3α-hydroxy-2β-(6-(2-hydroxy-Z-cyclopentylidine]-4-methyl-1E,4E-hexadienyl]-5-oxo-1α-cyclopentyl]-4Z-heptenoate.

5. A compound of claim 1 having the following formula

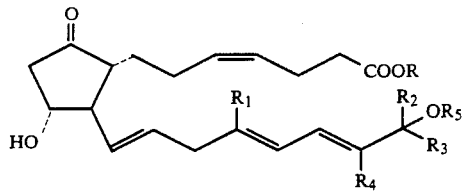

wherein R is alkyl having 1 to 6 carbon atoms; $R_1$ is alkyl having 1 to 6 carbon atoms; $R_2$, $R_3$ and $R_4$ are each independently hydrogen or alkyl having 1 to 4 carbon atoms; and $R_5$ is hydrogen, alkyl having 1 to 4 carbon atoms or acyl which is represented by the following formula

wherein $R_6$ is alkyl having 1 to 6 carbon atoms.

6. A compound of claim 5 which is
 (±)-methyl 7-[3α-hydroxy-2β-(8-hydroxy-4,8-dimethyl-1E,4,6-nonatrienyl)-5-oxo-1α-cyclopentyl]-4Z-heptenoate.

7. A compound of claim 5 which is
 (±)-methyl 7-[3α-hydroxy-2β-(8-methoxy-4,8-dimethyl-1E,4,6-nonatrienyl)-5-oxo-1α-cyclopentyl]-4Z-heptenoate.

8. A pharmaceutical composition useful for treating peptic ulcer disease in mammals comprising at least one compound according to claim 1, together with one or more non-toxic pharmaceutically acceptable carriers.

9. A pharmaceutical composition according to claim 8 wherein said compound is selected from the group consisting of
 (±)-methyl 7-[3α-hydroxy-2β-(8-hydroxy-4,8-dimethyl-1E,4,6-nonatrienyl)-5-oxo-1α-cyclopentyl]-4Z-heptenoate,
 (±)-methyl 7-[3α-hydroxy-2β-(8-methoxy-4,8-dimethyl-1E,4,6-nonatrienyl)-5-oxo-1α-cyclopentyl]-4Z-heptenoate,
 (±)-methyl 7-[3α-hydroxy-2β-(6-(2-hydroxy-Z-cyclopentylidine]-4-methyl-1E,4E-hexadienyl]-5-oxo-1α-cyclopentyl]-4Z-heptenoate, and
 (±)-methyl 7-[2β-(2-(acetyloxy)-Z-cyclopentylidine]-4-methyl-1E,4E-hexadienyl]-3α-hydroxy-5-oxo-1α-cyclopentyl]-4Z-heptenoate.

10. A method for treating peptic ulcer disease in mammals comprising administering a therapeutically effective dose of at least one compound of claim 1 to a mammal in need of such treatment.

11. A method according to claim 10 wherein said compound is selected from the group consisting of
 (±)-methyl 7-[3α-hydroxy-2β-(8-hydroxy-4,8-dimethyl-1E,4,6-nonatrienyl)-5-oxo-1α-cyclopentyl]-4Z-heptenoate,
 (±)-methyl 7-[3α-hydroxy-2β-(8-methoxy-4,8-dimethyl-1E,4,6-nonatrienyl)-5-oxo-1α-cyclopentyl]-4Z-heptenoate,
 (±)-methyl 7-[3α-hydroxy-2β-(6-(2-hydroxy-Z-cyclopentylidine]-4-methyl-1E,4E-hexadienyl]-5-oxo-1α-cyclopentyl]-4Z-heptenoate, and
 (±)-methyl 7-[2β-(6-(2-(acetyloxy)-Z-cyclopentylidine]-4-methyl-1E,4E-hexadienyl]-3α-hydroxy-5-oxo-1α-cyclopentyl]-4Z-heptenoate.

* * * * *

UNITED STATES PATENT AND TRADEMARK OFFICE
CERTIFICATE OF CORRECTION

PATENT NO.   : 5,089,524
DATED        : February 18, 1992
INVENTOR(S)  : Paul W. Collins, et al.

It is certified that error appears in the above-identified patent and that said Letters Patent is hereby corrected as shown below:

Column 1, line 67, reading "I to 6" should read -- 1 to 6 --.

Column 10, line 61, reading "C-16." should read -- C-16 --.

Column 12, line 5, should read -- Compound A --.

Column 12, line 17, should read -- Compound B --.

Column 14, line 49, reading "7-[2ß-(2-(acetyloxy)" should read -- 7-[2ß-(6-(2-(acetyloxy) --.

Signed and Sealed this

Fourteenth Day of September, 1993

Attest:

BRUCE LEHMAN

Attesting Officer

Commissioner of Patents and Trademarks